(12) United States Patent
Hosokawa et al.

(10) Patent No.: US 6,827,944 B2
(45) Date of Patent: Dec. 7, 2004

(54) PERCUTANEOUS ADMINISTRATION PREPARATIONS

(75) Inventors: Masaru Hosokawa, Tokyo (JP); Kumiko Shimizu, Tokyo (JP); Toshio Uesaka, Tokyo (JP); Ichiro Sugai, Tokyo (JP); Shinobu Mori, Ichikai-machi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/926,394

(22) PCT Filed: Feb. 23, 2001

(86) PCT No.: PCT/JP01/01345

§ 371 (c)(1),
(2), (4) Date: Oct. 25, 2001

(87) PCT Pub. No.: WO01/64184

PCT Pub. Date: Sep. 7, 2001

(65) Prior Publication Data

US 2003/0035826 A1 Feb. 20, 2003

(30) Foreign Application Priority Data

Feb. 29, 2000 (JP) .......................................... 2000-053095

(51) Int. Cl.[7] ............................ A61K 47/30; A61K 9/70
(52) U.S. Cl. ..................................... 424/449; 514/772.3
(58) Field of Search ........................ 424/449; 514/772.3

(56) References Cited

U.S. PATENT DOCUMENTS 5,240,995 A   8/1993   Gyory et al.

FOREIGN PATENT DOCUMENTS

| EP | 0 326 278 | | 8/1989 |
|---|---|---|---|
| EP | 0 524 612 | | 1/1993 |
| EP | 0 640 643 | | 3/1995 |
| EP | 0 863 172 | | 9/1998 |
| JP | 30-99 | | 1/1955 |
| JP | 60-123416 | * | 5/1985 |
| JP | 60-123416 | | 7/1985 |
| JP | 62-240612 | * | 10/1987 |
| JP | 2-258718 | | 10/1990 |
| JP | 3-112926 | | 5/1991 |
| JP | 3-11530 | * | 11/1991 |
| JP | 3-111530 | | 11/1991 |
| JP | 5-112423 | * | 5/1993 |
| JP | 6-507422 | | 8/1994 |
| JP | 9-291020 | | 11/1997 |
| JP | 10-226637 | | 8/1998 |
| JP | 2000-44476 | * | 2/2000 |

* cited by examiner

Primary Examiner—Carlos A. Azpuru
(74) Attorney, Agent, or Firm—Oblon, Spivak, McClelland, Maier & Neustadt, P.C.

(57) ABSTRACT

Provided is a composition for percutaneous administration containing a mixture of polymers forming a surface-segregated film, and (B) an active ingredient. The composition provides excellent percutaneous absorption efficacy of the active ingredient, particularly, a water-soluble active ingredient, has excellent feeling and is convenient to use.

21 Claims, 1 Drawing Sheet

PERCUTANEOUS ADMINISTRATION PREPARATIONS

TECHNICAL FIELD

The present invention relates to a composition for percutaneous administration which is particularly useful for percutaneous administration of a water soluble active ingredient and is excellent in feeling upon use and convenient to use.

BACKGROUND ART

Known methods for administration of pharmacological active ingredients are percutaneous administration, oral administration, injection, and the like. In particular, percutaneous administration is commonly used to decrease degradation in digestive tracts or first pass effect compared with oral administration, to reduce pain or burden given to patients compared with injection, and to continue administration for long hours. However, the skin essentially serves as a barrier for preventing invasion of foreign substances from the outside or evaporation of moisture in the body. The permeability of skin is lower than that of the general biomembrane.

A cataplasm using a hydrous gel preparation is one example of a means permitting efficient percutaneous absorption of pharmacological active ingredients. Accelerating efficacy of percutaneous absorption of the cataplasm is based on hydration and expansion of most outer layer of the epidermis, which is the horny cell layer of the skin and serves as a barrier of percutaneous absorption.

Since a cataplasm is formed by applying a hydrous gel containing an active ingredient to a backing material such as nonwoven cloth, it has suitable thickness and therefore lacks flexibility. In addition, adhesion of the hydrous gel layer to the skin is insufficient. As a result, it causes uncomfortable feeling during use, easily peels off from the skin by failing to move, and fails to provide sufficient acceleration of percutaneous absorption.

A composition for percutaneous administration containing a substance softening or hydrating the keratin layer such as urea or polyol has been proposed. However, efficacy of percutaneous absorption of active ingredients is still insufficient.

An object of the present invention is therefore to provide a composition for percutaneous administration which exerts an excellent percutaneous absorption performance of an active ingredient, has excellent feeling and is convenient to use.

DISCLOSURE OF THE INVENTION

The inventors have found that a composition for percutaneous administration comprising a polymer mixture which forms a surface-segregated film and an active ingredient provides efficient percutaneous absorption of an active ingredient when applied to the skin, has excellent feeling and is convenient to use.

The present invention therefore provides a composition for percutaneous administration comprising the following components (A) and (B):

(A) a polymer mixture which forms a surface-segregated film; and (B) an active ingredient.

BEST MODE FOR CARRYING OUT THE INVENTION

Figure 1:
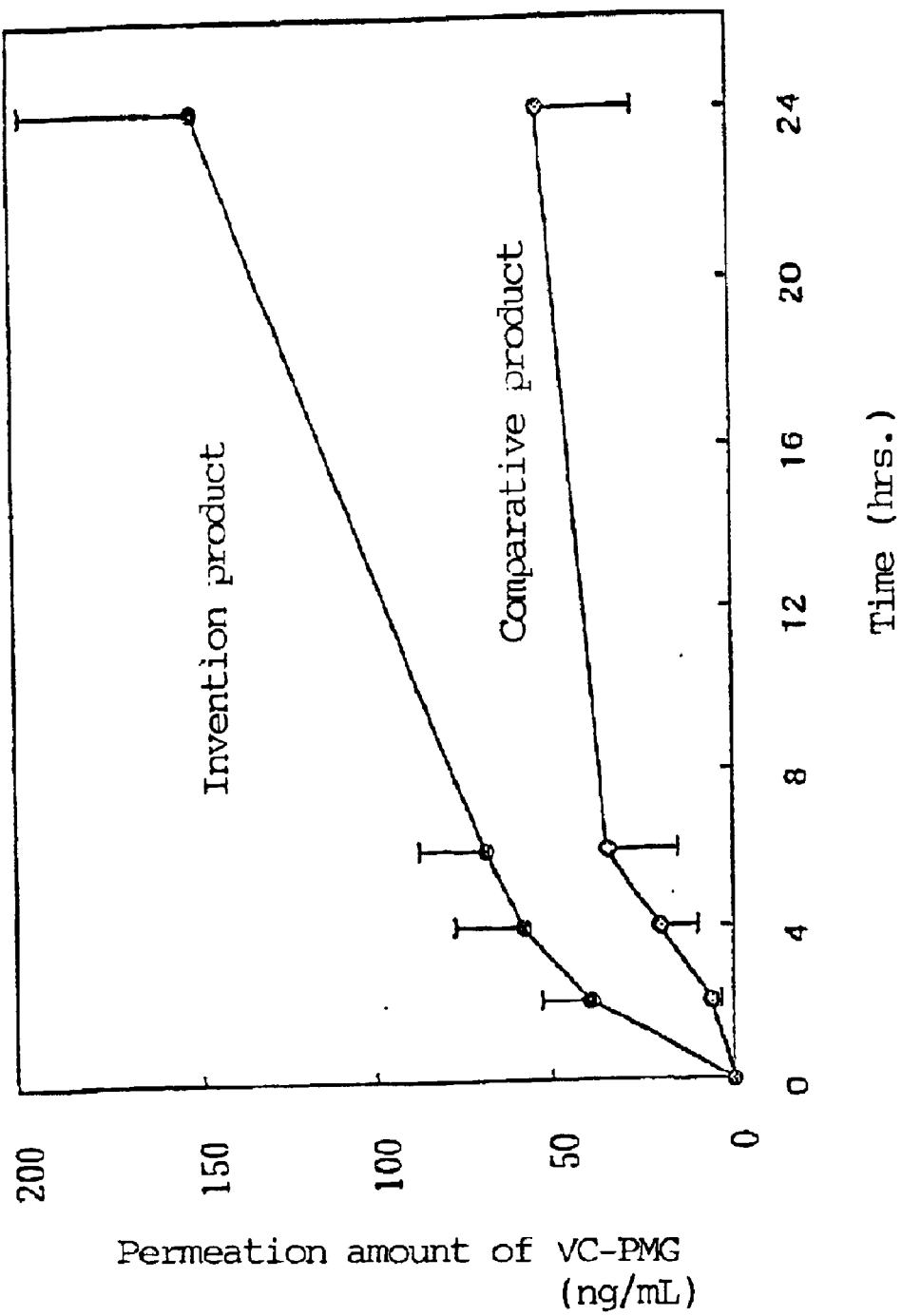
FIG. 1 illustrates the amount of a composition for percutaneous absorption of VC-PMG.

In the present invention, the term "surface-segregated film" means a film whose component has been partially segregated in the vicinity of the film surface. This surface segregation phenomenon can be observed by a surface analyzer such as FT-IR-ATR (Fourier Transform Infrared Spectrophotometer—Attenuated Total Reflection), XPS (X-ray Photoelectron Spectroscopy), or EDX (Energy Dispersion X-ray analysis) or an electron microscope such as TEM (Transmission Electron Microscope).

In the present invention, such surface segregation is caused by a composition comprising a mixture of at least two polymers having different properties. A film formed from a composition containing at least two polymers having different surface tension has a segregated surface, because owing to lowering in the surface energy of the film, a polymer component having lower surface tension $\gamma$ is segregated preferentially on the surface.

Preferably, such a polymer mixture has $\Delta\gamma$ of 3 mN/m or greater, especially 5 to 60 mN/m, which is a difference of the surface tension between two of these polymers, the maximum surface tension $\gamma_2$ and minimum surface tension $\gamma_1$.

First, contact angles (20°) of water and ethylene glycol on the film surface of the polymer prepared in a manner known per se in the art are measured, then surface tension is determined in accordance with the method of Hata, etc. (Journal of the Adhesion Society of Japan, 8(3), 9(1972)). When liquid (L) is contacted with the surface of polymer film (S) at a contact angle of $\theta$, the following equation can be established between surface tension and interfacial tension.

$$\gamma_S - \gamma_{SL} = \gamma_L \cos\theta \tag{1}$$

$$\gamma_{SL} = \gamma_L + \gamma_S - 2\sqrt{\gamma_S^d \times \gamma_L^d} - 2\sqrt{\gamma_S^p \times \gamma_L^p} \tag{2}$$

$$\gamma_S = \gamma_S^d + \gamma_S^p \tag{3}$$

$$\gamma_L = \gamma_L^d + \gamma_L^p \tag{4}$$

(wherein, $\gamma_s$ represents surface tension of the polymer film, $\gamma_{SL}$ represents the interfacial tension between the polymer film and liquid, $\gamma_L$ represents the surface tension of the liquid, $\gamma_S^d$, $\gamma_L^d$ represent non-polar sections of the surface tension of the polymer film and liquid, respectively, and $\gamma_S^P$, $\gamma_L^P$ represent polar sections of the surface tension of the polymer film and liquid, respectively).

Here, the equations (1) and (2) lead to the following equation (5):

$$\gamma_L + \gamma_L \cos\theta = 2\sqrt{\gamma_S^d \times \gamma_L^d} + 2\sqrt{\gamma_S^P \times \gamma_L^P} \tag{5}$$

The surface tension at 20° C. is as follows: in the case of water, $\gamma_L$=72.0 mN/m, $\gamma_L^d$=23.2 mN/m and $\gamma_L^P$=48.8 mN/m, while in the case of ethylene glycol, $\gamma_L$=48.9 mN/m, $\gamma_L^d$=33.4 mN/m and $\gamma_L^P$=15.5 mN/m. These values and the data of contact angle are substituted for the above equation (5) to determine $\gamma_s^d$ and $\gamma_s^P$, whereby $\gamma_s$ is available from the equation (3).

The component (A) includes a mixture of polymers forming a surface-segregated film. The advantage of the present invention is exhibited fully by selecting two polymers, for example, which have different surface tension so that the $\Delta\gamma$ will be 3 mN/m or greater, especially 5 to 60 mN/m. Such polymers are selected widely from the combination of a hydrophobic polymer and a hydrophilic polymer. Preferred combination of a hydrophobic polymer and a hydrophilic polymer is described below. The weight ratio of a hydrophobic polymer to a hydrophilic polymer preferably ranges from 5:95 to 95:5, especially 15:85 to 85:15 with regard to surface segregation.

As a hydrophobic polymer, those having a surface tension of 10 to 45 mN/m, especially 10 to 40 mN/m are preferred. Examples include film-forming silicone polymers and polymers having a fluorinated carbon chain. In addition, those taking a solid form at normal temperature and normal pressure but being soluble or dispersible in a volatile solvent are preferred for facilitating formulation.

Examples of the silicone polymer include oxazoline-modified organopolysiloxanes, vinyl copolymers containing a polysiloxane macromer, organopolysiloxanes having a sugar residue, alkyl-modified organopolysiloxanes and high polymerization organopolysiloxanes (as described, for example, in Japanese Patent Application Laid-Open No. 09-291020, Japanese Patent Application Laid-Open No. 06-145023, Japanese Language Laid-Open Publication No. 09-501728 (=WO95/06078), and "Fragrance Journal, 21(12), 56(1993)", Ibid, 24(12), 21–26(1996)).)

Preferred oxazoline-modified organopolysiloxanes are organopolysiloxanes (Japanese Patent Application Laid-Open No. 09-291020) comprising an organopolysiloxane segment (a) and a segment derived from open-ring polymerization of an oxazoline monomer, that is, a poly(N-acylalkyleneimine) segment which is bonded to the segment (a) at the end or side chain in the molecule thereof via a hetero-atom-containing alkylene group and consists of repeating units represented by the following formula (1):

(wherein, $R^1$ represents a hydrogen atom, a $C_{1-22}$ alkyl group, a cycloalkyl group, an aralkyl group or an aryl group, and k stands for 2 or 3), wherein the weight average molecular weight ranges from 50,000 to 500,000 and a weight ratio of (a) to (b) ranges from 98:2 to 40:60. The polystyrene equivalent weight average molecular weight is determined by gel permeation liquid chromatography (GPC) using chloroform as a developing solvent.

Examples of the polymer having a fluorinated carbon chain include homopolymers of a fluorine-containing vinyl monomer, copolymers containing a fluorine-containing vinyl monomer as a constituent (Japanese Patent Application Laid-Open No. 11-100306) and vinylidene fluoride—hexafluoroacetone copolymer.

Examples of the fluorine-containing vinyl monomer include fluoroalkyl (meth)acrylates, fluoroalkyl (meth) acrylic amide esters, fluoroalkyl vinyl ethers and fluoro-α-olefins, of which (meth)acrylates having a fluoroalkyl group (having 6 to 12 carbon atoms) are preferred. As the fluoroalkyl group, polyfluoroalkyl and perfluoroalkyl groups can be exemplified.

As the monomer copolymerizable with the fluorine-containing vinyl monomer, preferred are alkyl (meth) acrylates having a linear or branched alkyl group having at least 8 carbon atoms and/or dimethylpolysiloxane compounds having, at one end of the molecular chain, a radical polymerizable group. Fumarate esters can also be given as another example.

As the hydrophobic polymer, two or more hydrophobic polymers may be mixed. The composition contains the hydrophobic polymer in an amount of 0.001 to 30 wt. % (which will hereinafter be called "%", simply), preferably 0.005 to 20%, more preferably 0.01 to 10%. Oxazoline-modified organopolysiloxanes are particularly preferred.

As the hydrophilic polymer, its surface tension ranging from 30 to 70 mN/m, especially 40 to 70 mN/m is preferred. Examples include natural or synthetic film-forming polymers, more specifically, polysaccharides such as acidic heteropolysaccharides, mucopolysaccharides and cellulose derivatives, polypeptides, hydroxyl-containing polymers such as polyvinyl alcohol and polyethylene glycol, and water-soluble polymers such as cationic-group-containing polymers.

More specific examples include acidic heteropolysaccharides derived from the callus of plants belonging to Polianthes L., hyaluronic acid, arabic gum, guar gum, xanthan gum, pectin, locust bean gum, carrageenan, maltotriose, collagen and derivatives thereof, pullulan, chitin and derivatives thereof, chitosan and derivatives thereof, cationated cellulose, carboxymethyl cellulose, methyl cellulose, ethyl cellulose, hydroxyethyl cellulose, hydroxypropyl cellulose, hydroxypropylmethyl cellulose, polyvinyl alcohol, polyethylene glycol and poly (methacryloyloxyethyltrimethylammonium chloride) (as described, for example, in Fragrance Journal, 21(12), 13–73 (1993)).

Among the hydrophilic polymers, water-soluble polymers having a polystyrene equivalent weight average molecular weight of 4000 to 500000 as measured by GPC, especially 10000 to 500000 are preferred. More specifically, polyvinyl alcohol, polyethylene glycol, collagen and derivatives thereof, pullulan, chitin and derivatives thereof, and chitosan and derivatives thereof are preferred, with polyvinyl alcohol being especially preferred.

Two or more hydrophilic polymers may be mixed. The composition contains the hydrophilic polymers in an amount of 0.001 to 30%, especially 0.005 to 20%, more preferably 0.01 to 10%.

As the combination of polymers forming a surface-segregated film, that of a silicone polymer or a polymer having a fluorinated carbon chain and a water soluble polymer, especially that of an oxazoline-modified organopolysiloxane and polyvinyl alcohol is preferred.

Although no particular limitation is imposed on the component (B) insofar as it is a substance exhibiting effects such as corium firming, whitening, blood-circulation stimulating, lipolysis accelerating or anti-inflammatory effects, water-soluble substances are desired from the viewpoint of percutaneous absorption. A substance having markedly small solubility in water may be employed. Specific examples include plant extracts, animal extracts, guanidine derivatives, catecholamines, amino acids, vitamins, hormones and organic acids.

Examples of the plant extracts include those having corium firming effects *Ginkgo biloba* (gingko), Foeniculi Fructus (fennel), kiwi, *Morus bombycis* (mulberry), *Gentiana lutea* (gentian), red algae, *Arctium lappa* (burdock), *Salvia officinalis* (sage), *Lentinus edodes* (shiitake mushroom), *Perilla frutescens* (perilla), Filipendula Multijuga, *Fucus vesiculosis* (bladderwrack, sea weed), peach kernel, *Panax ginseng* (carrot), *Allium sativum* (garlic), *Poria cocos* (poria), *Humulus lupulus* (hops), Mutan Cortex (Moutan Bark), *Pimpinella major, Lactuca sative* (lettuce), *Astragalus membranaceous* (astragalus) and *Rosmarinus officinalis* (rosemary); those having whitening effects such as *Prunus amygdalus* (almond), *Althea officinale* (althea), aloe, Rosae Fructus (rose fruit, or *Rosa multiflora*), *Scuttelaria baicalensis* (Huang qin), Puerariae Radix (Pueraria Root, or *Pueraria lobata*), Chamomillae Flos (German chamomile), *Gardenia jasminoides* (zhii zi, Gardeniae Fructus), *Sophora flavescens* Aiton (Sophorae Radix), chlorella, rice bran, *Paeoniae lactiflora* (white peony), ziyu (*Sanguisorba officinalis*, burnet), *Morus alba* (sang bai pi, mulberry), *Glycine max* (soybean), *Camellia sinensis* (tea), Carthami Flos (safflower), *Aesculus hippocastanum* (horse chestnut), *Melissa officinalis* (lemon balm) and Coicis Semen (Coix lacryma-jobi var. ma-yuen); those having blood circulation accelerating effects such as *Angelica keisukei*, *Arnica montana* (arnica), *Foeniculum officinale* (fennel), *Isodon japonicus* Hara (Isodonis Herba), Daucus Carota (carrot), *Oryza sativa* (rice), *Crataegus cuneata* (Japanese howthorn), *Acorus calamus* (sweet flag), *Crataegus oxycantha* (howthorn), *Juniperus communis*, *Ligusticum wallichii* (Chinese lovage), Swertiae Herba (Swertia Herb), *Thymus vulgaris* (garden thyme), *Citrus reticulata* (Citrus unshiu), *Capsicum tincture*, *Angelicae sinensis* (angelica), *Aurantii Pericarpium* (bitter orange peel), *Ruscus aculeatus* (butcher's bloom), *Vitis vinifera* (grape), *Tilia japonica* (lime), *Citrus junos* and *Rosa canina* (rose hip); those having lipolysis accelerating effects, for example, thistles such as *Cephalonoplos segetnum* (Bieb.) Kitam. and *Cirsium japonicum* DC (Japanese Patent Application Laid-Open No. 08-301780 (=U.S. Pat. No. 5,698, 199)), caffeine, Cinnamomi Cortex (cinnamon bark) and *Eriobotrya japonica* Lindl. (loquat); those having anti-inflammatory effects Gambir, Echinacea, Phellodendri Cortex (amur cork tree or *Phellodendron amurense*), *Hypericum perforatum* (St. John's wort), *Citrus sinensis* (orange), *Valeriana fauriei* Briquet, *Artemisia capillaris* Thunb., *Cucumis sativus* (cucumber), Geranii Herba (Geranium Herb), *Lithospermum erythrorhizon* Sieb. et Zucc., *Hedera helix*, *Achillea millefolium* (yarrow), *Ziziphus jujuba* (Chinese dates), *Calendula officinalis* (pot marigold), *Houttuynia cordata* (Houttuyniae Herba, Houttuynia Herba), *Potentilla erecta*, *Petroselinum crispum* (parsley), *Parietaria officinalis*, *Santalum album* (sandalwood), *Prunus persica* (peach), *Centaurea cyanus* (cornflower), *Eucalyptus globulus* (eucalyptus) and *Lavandula angustifolia* (lavender); those having hair-growth accelerating effects such as *Persea americana* (avocado), *Aloe vera* (aloe), *Nasturtium officinalis* (watercress), *Symphytum officinale* (comfrey), *Asarum sieboldii* (wild ginger), *Xanthoxyum piperitum* (Japan pepper), *Rehmannia glutinosa* (di huang), *Mentha piperita* (peppermint), *Syzygium aromaticum* (clove), *Tussilago farfara* (coltsfoot) and *Haematoxylum campechianum* (logwood); and those having anti-aging effects such as Oolong tea, *Cinchona succirubra* (peruvian bark), *Betula verrucosa* (birch) and *Glechoma hederacea* (ground ivy); while examples of the animal extracts include placenta extract having whitening effects, milk and royal jelly having blood circulation accelerating effects, honey having anti-inflammatory effects and pearl protein having cell activating action (for example, as described in Fragrance Journal 23(8), 41 to 47(1995), Ibid 24(8), 62 to 67(1996)).

As the component (b), those exemplified above may be used either singly or in combination. It is preferably added to a composition in an amount of 0.00001 to 30%, especially 0.0001 to 20%. When the active ingredient is a plant or animal extract, the amount does not include the extracting solvent but its solid content. As the extract, commercially available ones in the liquid form may be used as is.

The composition for percutaneous administration of the present invention can be prepared by adding the active ingredient in a solution or dispersion obtained by dissolving or dispersing at least two polymers forming a surface-segregated film to a volatile solvent.

As the volatile solvent, those having a boiling point of 210° C. or less, preferably 40 to 110° C. are preferred. Water and lower alcohols (having 1 to 3 carbon atoms) are more preferred, with water and ethanol being especially preferred. The volatile solvent is preferably added to the composition in an amount of 30 to 98%, especially 50 to 95%.

When the composition for percutaneous administration of the present invention is applied to the skin, a film is formed with the polymer having lower surface tension being surface-segregated on the air interface side.

The composition for percutaneous administration of the present invention is prepared in a conventional manner by adding various optional components ordinarily employed for cosmetics, quasi-drugs or drugs within an extent not impairing the advantage of the present invention.

No particular limitation is imposed on the various optional components usable here, but examples include oleaginous agents, more specifically, hydrocarbons, ester oils, higher fatty acids, higher alcohols, naturally extracted sphingosine derivatives and synthetic ceramide analogs (Japanese Patent Application Laid-Open No. 62-228048 (=EP-A-227994), Japanese Patent Application Laid-Open No. 08-319263 (=U.S. Pat. No. 5,863,945)), polyhydric alcohols, thickeners, fatty acids, surfactants, powders, clay minerals, inorganic salts, pH regulators, chelating agents, antioxidants, antiseptics, colorants, ultraviolet absorbers and perfumes.

Although the composition for percutaneous administration of the present invention can be prepared in various forms such as solution, paste, gel, emulsion and dispersion, the solution, paste and gel in which the active ingredient has been dissolved are preferred for percutaneous absorption. The composition for percutaneous administration of the present invention is preferred to have a viscosity of 0.01 to 200 Pa·s (25° C.), preferably 0.1 to 100 Pa·s from the viewpoint of convenient use.

EXAMPLE

Example 1

A composition for percutaneous administration (invention product) was obtained in a gel form by stirring and mixing the component (2) having the composition as shown in Table 1 at 80° C., cooling the resulting solution to room temperature, and mixing it with the component (1) mixed at room temperature in advance. As a comparative product, the composition as shown in Table 1 was applied to a nonwoven cloth, whereby a cataplasm was prepared. Its viscosity as measured at 25° C. by a B8L viscometer (manufactured by Tokimec, Inc.) under the conditions of a No. 3 rotor, 12 rpm and 60 seconds was 5.0 Pa·s.

TABLE 1

| Component | (%) Invention product | Comparative product |
|---|---|---|
| Component (1): | | |
| Oxazoline-modified organopolysiloxane (30% ethanol solution)[1] | 3.78 | 0 |
| Ethanol | 5 | 0 |
| Succinic acid | 0.1 | 0 |
| Magnesium ascorbyl L-phosphate | 0.05 | 0.05 |
| Disodium edatate | 0.2 | 0.2 |
| l-Menthol | 0.1 | 0 |

TABLE 1-continued

| | (%) | |
|---|---|---|
| Component | Invention product | Comparative product |
| Component (2): | | |
| Polyvinyl alcohol[2] | 0.48 | 0 |
| Hydroxyethyl cellulose | 1 | 0 |
| Propylene glycol | 8 | 0 |
| Methyl paraoxybenzoate | 0.2 | 0.2 |
| Purified water | Balance | Balance |
| Polyacrylic acid | 0 | 1.5 |
| Sodium polyacrylate | 0 | 5.5 |
| Dried aluminum hydroxide gel | 0 | 0.2 |
| Silicic anhydride | 0 | 2 |
| Glycerin | 0 | 35 |

[1]Dimethylsiloxane/N-propionylethyleneimine copolymer (Preparation Example 2 of Japanese Patent Application Laid-Open No. 09-291020) surface tension: 37.9 mN/m
[2]"GOHSENOL EG-30" (product of Nippon Synthetic Chemical Industry Co., Ltd.) surface tension: 47.3 mN/m (1) Test Method on Percutaneous Absorption:

Magnesium ascorbyl L-phosphate (VC-PMG) employed as a water-soluble active ingredient was added to each composition as shown in Table 1.

The abdominal skin of male Wistar rats 9 to 10 weeks of age shaven in advance was enucleated together with their subcutaneous tissue and was divided by a median line. The skin piece was mounted on an improved Franz diffusion cell (inner diameter: 2.5 cm; skin area: 4.9 cm$^2$). After physiological saline was filled in a receptor tank, stirring was conducted continuously by a stirrer. The surface of the skin was treated in a warm-water bath (water of 38° C. for 10 minutes) and then, a predetermined amount (40 mg) of the preparation was applied to the skin surface. It was allowed to stand under the circumstance of 30° C. and 65% RH. At regular intervals, 50 µL portions were sampled from the receptor tank. The VC-PMG in physiological saline which had permeated through the skin was analyzed and its amount was determined by HPLC. The results are shown in FIG. 1.

The determination of the amount of VC-PMG by HPLC was conducted by ion column chromatography using a reversed phase column under the following conditions:
HPLC column: Lichrosorb RP-18 4.5Ø×150 mm/5 µm
Eluent: 0.08M acetic acid/sodium acetate
  2.8 mM Tetra-n-butylammonium hydrogensulfate
  0.1 mM EDTA-2Na
  2% MeOH aq
Flow rate: 0.8 mL/min
Temperature: 30° C.
Detection: 260 nm As apparent from FIG. 1, the invention product was excellent in percutaneous absorption of VC-PMG.

(2) Evaluation of Feeling Upon Use and Convenience:

Feeling upon use and convenience of each preparation were evaluated by a panel of 20 female experts who applied it to their abdomen (applied region: 10 cm×10 cm). The feeling upon use was ranked as 5 points when it was good, 4 points when slightly good, 3 points when neither good nor bad, 2 points when not so favorable and 1 point when not favorable, while the convenience was ranked as 5 points when the preparation was judged convenient, 4 points when judged slightly convenient, 3 points when judged neither convenient nor inconvenient, 2 points when judged not so convenient and 1 point when judged inconvenient. Evaluation was expressed by the average of 20 experts. The results are shown in Table 2.

TABLE 2

| Item to be evaluated | Invention product | Comparative product |
|---|---|---|
| Feeling upon use | 4.5 | 3.0 |
| Convenience | 5.0 | 2.0 |

As is apparent from Table 2, the invention product was superior to the cataplasm of Comparative product in both feeling upon use and convenience.

Example 2

| (Component) | (%) |
|---|---|
| Oxazoline-modified organopolysiloxane (30% ethanol solution)[3] | 3.0 |
| Polyvinyl alcohol[4] | 1.0 |
| Propylene glycol | 5.0 |
| Hydroxyethyl cellulose | 0.7 |
| 2-(2-Hydroxyethoxy)ethylguanidine succinate | 2.5 |
| Extract of *Sanguisorba oifficinalis* (ziyu) | 1.0 |
| Extract of *Fucus vesiculosis* (bladderwrack) | 1.0 |
| Ethanol | 5.0 |
| Purified water | Balance |

[3], [4]Substances similar to those employed in Example 1 were used (this will apply equally hereinafter)

Viscosity: 1.5 Pa·s

Example 3

| (Component) | (%) |
|---|---|
| Oxazoline-modified organopolysiloxane (30% ethanol solution) | 3.5 |
| Polyvinyl alcohol | 0.5 |
| Succinic acid | 0.1 |
| 1-(2-hydroxyethylamino)-3-isostearyl oxy-2-propanol | 0.2 |
| Glycerin | 4.0 |
| Guar gum | 0.8 |
| Extract of *Eucalyptus globulus* (eucalyptus) | 1.5 |
| Extract of *Tilia japonica* (lime) | 1.0 |
| Disodium edatate | 0.2 |
| Methylparaben | 0.2 |
| Ethanol | 10.0 |
| Purified water | Balance |
| Viscosity: 2.16 Pa · s | |

Example 4

| (Component) | (%) |
|---|---|
| Oxazoline-modified organopolysiloxane (30% ethanol solution) | 3.5 |
| Polyvinyl alcohol | 0.5 |
| Succinic acid | 0.1 |
| Propylene glycol | 5.0 |
| Xanthan gum | 0.8 |
| Extract of *Chamomillae Flos* (German chamomile) | 0.5 |
| Extract of Thistle | 1.0 |
| Extract of *Fucus vesiculosis* (bladderwrack) | 1.0 |
| Caffeine | 0.2 |
| Disodium edatate | 0.2 |
| Methylparaben | 0.2 |
| Ethanol | 10.0 |
| Purified water | Balance |
| Viscosity: 3.35 Pa · s | |

Example 5

| (Component) | (%) |
|---|---|
| Oxazoline-modified organopolysiloxane (30% ethanol solution) | 3.5 |
| Pollulan[5] | 1.0 |
| Propylene glycol | 4.0 |
| Hydroxyethylcellulose hydroxypropyl cellulose stearyl ether sodium hydroxypropylsulfonate | 0.8 |
| Extract of Althea Officinalis (althea) | 0.8 |
| Ascorbic acid | 1.0 |
| Methylparaben | 0.2 |
| Ethanol | 10.0 |
| Purified water | Balance |

[5]"Pullulan PI-20" (product of Hayashibara Group), surface tension: 47 mN/m

Viscosity: 17.1 Pa·s

Example 6

| (Component) | (%) |
|---|---|
| Oxazoline-modified organopolysiloxane (30% ethanol solution) | 3.5 |
| Polyethylene glycol[6] | 0.5 |
| Glycerin | 4.0 |
| Synthetic ceramide analog[7] | 0.1 |
| Phytosphingosine[8] | 0.2 |
| Polyoxyethylene sorbitan monostearate (20 E.O.) | 0.7 |
| Sorbitan monostearate | 0.3 |
| Cholesterol | 0.3 |
| Xanthan gum | 0.8 |
| Extract of *Sanguisorba officinalis* (ziyu) | 1.0 |
| Disodium edatate | 0.2 |
| Methylparaben | 0.2 |
| Ethanol | 10.0 |
| Purified water | Balance |

[6]"Polyox N-3000" (product of Amerchol Corporation, molecular weight: 400000), surface tension: 45.5 dyn/cm
[7]The amide derivative (1a) as described in Example 1 of Japanese Patent Application Laid-Open No. 08-319263
[8]Phytosphingosine (product of Penta Farm)

Viscosity: 1.9 Pa·s

Compositions for percutaneous administration obtained in Examples 2 to 6 can be applied to any desired part of the body, are useful for percutaneous administration of a water soluble active ingredient, have excellent feeling and are convenient to use.

INDUSTRIAL APPLICABILITY

The composition for percutaneous administration of the present invention is excellent in percutaneous absorption of an active ingredient, particularly, a water-soluble active ingredient, has excellent feeling and is convenient to use.

What is claimed is:

1. A composition for percutaneous administration comprising:
   (A) a mixture of polymers forming a surface-segregated film, said polymers consisting of (A-1) a hydrophobic polymer which has a surface tension of 10 to 45 mN/m, takes solid form at normal temperature and normal pressure, and is soluble or dispersible in water and/or a lower alcohol solution, and (A-2) a hydrophilic polymer which has a surface tension of 30 to 70 mN/m;
   (B) a hydrophilic active ingredient selected from the group consisting of plant extracts, animal extracts, guanidine derivatives, catecholamines, amino acids, vitamins, and hormones; and
   (C) water and/or a lower alcohol.

2. The composition according to claim 1, wherein the component (A-1) is a silicone polymer or a polymer having a fluorinated carbon chain.

3. The composition according to claim 1, wherein the hydrophobic polymer (A-1) is an oxazoline-modified organopolysiloxane comprising:
   an organopolysiloxane segment (a) and a poly(N-acylalkyleneimine) segment (b) which is bonded to the segment (a) at the end or side chain in the molecule thereof via a hetero-atom-containing alkylene group and consists of repeating units represented by the following formula (1):

(1)

wherein, $R^1$ represents a hydrogen atom, a $C_{1-22}$ alkyl group, a cycloalkyl group, an aralkyl group or an aryl group, and k stands for 2 or 3, wherein the weight average molecular weight ranges from 50000 to 500000 and a weight ratio of segment (a) to segment (b) ranges from 98:2 to 40:60; and said oxazoline-modified organopolysiloxane takes solid form at normal temperature and normal pressure, and is soluble or dispersible in water and/or a lower alcohol solution.

4. The composition according to claim 1, wherein the hydrophilic polymer (A-2) is selected from the group consisting of polyvinyl alcohol, polyethylene glycol and pullulan.

5. The composition according to claim 1, wherein the weight ratio of the hydrophobic polymer (A-1) to the hydrophilic polymer (A-2) ranges from 5:95 to 95:5.

6. The composition according to claim 1, wherein the weight ratio of the hydrophobic polymer (A-1) to the hydrophilic polymer (A-2) ranges from 15:85 to 85:15.

7. The composition according to claim 1, wherein the concentration of the hydrophobic polymer (A-1) in the composition ranges from 0.001 to 30 wt %.

8. The composition according to claim 1, wherein the concentration of the hydrophobic polymer (A-1) in the composition ranges from 0.005 to 20 wt %.

9. The composition according to claim 1, wherein the concentration of the hydrophobic polymer (A-1) in the composition ranges from 0.01 to 10 wt %.

10. The composition according to claim 1, wherein the weight-average molecular weight of the hydrophilic polymer (A-2) ranges from 4000 to 500,000.

11. The composition according to claim 1, wherein the weight-average molecular weight of the hydrophilic polymer (A-2) ranges from 10,000 to 500,000.

12. The composition according to claim 1, wherein the concentration of the hydrophilic polymer (A-2) in the composition ranges from 0.00 1 to 30 wt %.

13. The composition according to claim 1, wherein the concentration of the hydrophilic polymer (A-2) in the composition ranges from 0.005 to 20 wt %.

14. The composition according to claim 1, wherein the concentration of the hydrophilic polymer (A-2) in the composition ranges from 0.01 to 10 wt %.

15. The composition according to claim 1, wherein the concentration of the hydrophilic active ingredient in the composition ranges from 0.00001 to 30 wt %.

16. The composition according to claim 1, wherein the concentration of the hydrophilic active ingredient in the composition ranges from 0.0001 to 20wt %.

17. The composition according to claim 1, wherein the water and/or a lower alcohol has a boiling point less than 210° C.

18. The composition according to claim 1, wherein the water and/or a lower alcohol has a boiling point ranging from 40 to 110° C.

19. The composition according to claim 1, wherein the concentration of the water and/or a lower alcohol in the composition ranges from 30 to 98 wt %.

20. The composition according to claim 1, wherein the concentration of the water and/or a lower alcohol in the composition ranges from 50 to 95 wt %.

21. A method for accelerating the percutaneous absorption of a hydrophilic active ingredient, which comprises applying the composition described in claim 1 to the skin of a subject in need thereof.

* * * * *